(12) United States Patent
Villard et al.

(10) Patent No.: US 9,891,095 B2
(45) Date of Patent: Feb. 13, 2018

(54) METHOD AND SYSTEM TO PROVIDE A PERSON WITH A PERSONALIZED ADVICE WITH REGARD TO HIS/HER WEIGHT

(71) Applicant: WITHINGS, Issy les Moulineaux (FR)

(72) Inventors: Joffrey Villard, Paris (FR); Guillaume Jeanne, Lagny sur Marne (FR)

(73) Assignee: WITHINGS, Issy les Moulineaux (FR)

( * ) Notice: Subject to any disclaimer, the term of this patent is extended or adjusted under 35 U.S.C. 154(b) by 120 days.

(21) Appl. No.: 14/520,612

(22) Filed: Oct. 22, 2014

(65) Prior Publication Data

US 2015/0107910 A1  Apr. 23, 2015

(30) Foreign Application Priority Data

Oct. 22, 2013 (FR) ..................... 13 60284

(51) Int. Cl.
| | |
|---|---|
| *G01G 19/50* | (2006.01) |
| *G09B 19/00* | (2006.01) |
| *G06F 19/00* | (2011.01) |
| *G01G 19/414* | (2006.01) |
| *G06Q 50/22* | (2012.01) |
| *G01G 23/37* | (2006.01) |

(52) U.S. Cl.
CPC ......... *G01G 19/50* (2013.01); *G01G 19/4146* (2013.01); *G01G 23/3728* (2013.01); *G06F 19/3418* (2013.01); *G06Q 50/22* (2013.01); *G09B 19/0092* (2013.01)

(58) Field of Classification Search
CPC . G01G 19/4146; G01G 19/50; G01G 23/3728
See application file for complete search history.

(56) References Cited

U.S. PATENT DOCUMENTS

| 5,673,691 A | 10/1997 | Philip et al. |
| 7,557,311 B2 * | 7/2009 | Umemoto ............ A61B 5/0537 |
| | | 177/25.16 |

(Continued)

FOREIGN PATENT DOCUMENTS

| FR | 2 910 155 A1 | 6/2008 |
| FR | 2 944 598 A1 | 10/2010 |
| WO | WO 2007/102708 A1 | 9/2007 |

OTHER PUBLICATIONS

Search report for related French Application No. 1360284; report dated Jul. 10, 2014.

*Primary Examiner* — Natalie Huls
(74) *Attorney, Agent, or Firm* — Miller, Matthias & Hull LLP

(57) ABSTRACT

A method for providing personalized recommendations to an individual, relating to monitoring his or her weight, comprising the steps of /a/ obtaining a plurality of prior weighings for the individual concerned, each weighing giving the total weight and the body fat percentage, /b/ deriving a characteristic curve (S1) for the individual by associating at least the total weight and the fat body mass, /c/ obtaining a target total weight (P2) for the user to achieve by the end of a target period, and therefore a target total weight change, /d/ deducing a target number of calories to burn, corresponding to target changes in the fat body mass and lean body mass deduced from the total weight change, /e/ providing the user with personalized instructions on exercise and/or diet.

12 Claims, 2 Drawing Sheets

(56) References Cited

U.S. PATENT DOCUMENTS

| | | | |
|---|---|---|---|
| 7,949,506 B1 | 5/2011 | Hill et al. | |
| 8,475,367 B1 * | 7/2013 | Yuen | G06F 19/3418 128/920 |
| 8,538,772 B2 * | 9/2013 | Sato | A61B 5/0537 705/2 |
| 8,541,700 B2 * | 9/2013 | Sato | G01G 23/3728 177/25.11 |
| 2003/0013982 A1 * | 1/2003 | Shimomura | A61B 5/0537 600/547 |
| 2003/0083589 A1 * | 5/2003 | Oguma | A61B 5/0537 600/547 |
| 2004/0225533 A1 * | 11/2004 | Cosentino | A61B 5/7475 705/3 |
| 2005/0247494 A1 * | 11/2005 | Montagnino | A61B 5/0537 177/60 |
| 2006/0015016 A1 * | 1/2006 | Thornton | A61B 5/00 600/300 |
| 2006/0259323 A1 * | 11/2006 | Chan | G06Q 50/22 705/2 |
| 2008/0051679 A1 * | 2/2008 | Maljanian | G01G 19/4146 600/587 |
| 2008/0154645 A1 * | 6/2008 | Takehara | A61B 5/0002 705/3 |
| 2014/0083779 A1 * | 3/2014 | Sharma | G01G 19/44 177/1 |
| 2014/0285491 A1 * | 9/2014 | Otsubo | A61B 5/742 345/440 |
| 2015/0093725 A1 * | 4/2015 | Baarman | G06F 19/3475 434/127 |
| 2015/0161911 A1 * | 6/2015 | Muto | G06F 17/30554 434/127 |

* cited by examiner

METHOD AND SYSTEM TO PROVIDE A PERSON WITH A PERSONALIZED ADVICE WITH REGARD TO HIS/HER WEIGHT

CROSS-REFERENCE TO RELATED APPLICATION

This application claims priority under the Paris Convention to French Patent Application No. 13 60284 filed on Oct. 22, 2013.

FIELD OF THE DISCLOSURE

The present invention relates to methods and systems for providing weight-related recommendations to an individual, said recommendations typically in the form of exercise instructions and/or diet instructions.

BACKGROUND OF THE DISCLOSURE

More particularly, the invention relates to a method and system for providing customized and personalized recommendations to an individual, particularly by using a series of weighings collected by a communicating electronic scale.

In the prior art, it is known to apply baseline calculations using, for example, Forbes equations which are based on statistical studies and where the main parameters are the age, height, weight, and gender of individuals who want to monitor their weight or lose weight.

Some of the proposed methods are intrusive and require measuring a parameter of a body fluid such as blood.

Weight loss systems are also known, for example from document U.S. Pat. No. 7,949,506, which recommend one or more amounts of physical activity and the intake of food supplements intended to cause weight loss. However, these systems require the user to enter a large number of parameters, which is tedious and discourages many users.

There is therefore a need to provide a simpler and non-intrusive solution for indicating to a user how to achieve a target weight that he or she has set, and to do so with the relevance of individualized and personalized recommendations.

SUMMARY OF THE DISCLOSURE

To this end, the invention proposes a method for providing personalized recommendations to an individual, relating to monitoring and/or controlling his or her weight, comprising the steps of:
/a/ obtaining a plurality of prior weighings of the individual concerned, each weighing giving the total weight and the body fat percentage,
/b/ deriving a characteristic curve for the individual by associating at least two of the following three quantities: total weight, fat body mass, and lean body mass, over at least one total weight range,
/c/ obtaining a target total weight for the user to be achieved by the end of a target period, and thus a target total weight change relative to the latest known total weight reading,
/d/ deducing from steps /b/ and /c/ a target number of calories to burn, corresponding to target changes in the fat body mass and lean body mass deduced from said total weight change by means of the characteristic curve,
/e/ providing the user with exercise and/or diet instructions, in particular based on said target number of calories to burn;

whereby the user can receive personalized recommendations for achieving the target weight. The personalization takes into account the characteristic curve of the individual and the recommendations are more relevant than if formulas based on a statistical set of individuals is used.

With these arrangements, the prior weighings of the individual are used in an intelligent way to provide personalized advice allowing the individual to reach his or her target weight. The recommendations are therefore more relevant and focused than if they were based on general statistical data.

In embodiments of the method according to the invention, one or more of the following arrangements may possibly be used.

First, step /a/ may further comprise:
/a1/ determining a current trend concerning the total weight of the individual, by means of the most recent weighings, and step /d/ may further comprise
/d1/ deducing, from the target total weight change, the change expected at the end of the target period, due to the current trend, the target number of calories to burn then being a relative target number of calories,
such that the instructions given to the user are instructions to change behaviour relative to recent habits (rather than absolute instructions). This eliminates the need to provide absolute instructions on diet and/or exercise; we simply provide instructions on changing habits, especially in terms of exercise.

Additional parameters could also be used, including the gender, age, and height of the individual, in converting, in step /e/, the target number of calories to burn into exercise duration for the individual concerned; whereby the exercise instructions are particularly well-targeted to the individual in question, whether the instructions concern walking, jogging, swimming, or any other physical activity.

In particular, the instructions may be provided in the form of a number of steps to be taken; whereby the user is informed of a simple physical activity allowing him or her to reach the target weight he or she has set; the instructions are, for example, daily.

In step /e/, instructions on changing habits in terms of an additional number of steps to be taken are added to the average daily number of steps taken in the past; such that the instructions on changing habits are converted into absolute instructions for daily walking exercise.

One can approximate the characteristic curve by a straight line within a habitual weight range of the user; so as to particularly simplify the calculations.

The invention also provides a system for implementing a method as described above, comprising:
a scale, configured to measure the total weight and the body fat percentage of an individual and to send the data to a remote unit,
a remote unit, capable of performing calculations, configured to collect and process the collected data originating from the scale, and formulate instructions for reaching a target weight for the individual at the end of a target period,
a personal device in relation to the individual (smartphone, tablet, personal activity monitor, etc.), for providing a visual indication of the instructions, whereby the user is provided with personalized instructions for an achievable goal, on a familiar interface.

In embodiments of the method according to the invention, one or more of the following arrangements may be used.

The remote unit may be a data server, providing substantial computing power which allows making precise calculations; algorithm updates are also facilitated by a centralized operation (even in a "cloud" type of distribution).

The remote unit may be a smart mobile device (smartphone, tablet, laptop); whereby the system (and also the method) can operate independently by means of objects in the user's immediate environment.

The remote unit can be combined with the personal device, for example a smartphone or tablet, whereby a system comprising only the scale and the personal device, for example a smart mobile device such as a smartphone or tablet, can implement the entire method.

The personal device may be a personal activity monitor and the instructions are displayed on it as a number of steps to be taken, such that the instructions are accessible to the user on the device most appropriate for his or her exercise or physical activity.

The personal device may consist of the scale itself. Scales with expanded functionalities able to implement the entire method can thus be offered.

Other features and advantages of the invention will be apparent from the following description of one of its embodiments, given by way of non-limiting example, with reference to the accompanying drawings.

BRIEF DESCRIPTION OF THE DRAWINGS

In the drawings.

In the various figures, the same references denote identical or similar elements.

DETAILED DESCRIPTION OF THE DISCLOSURE

Figure 1:
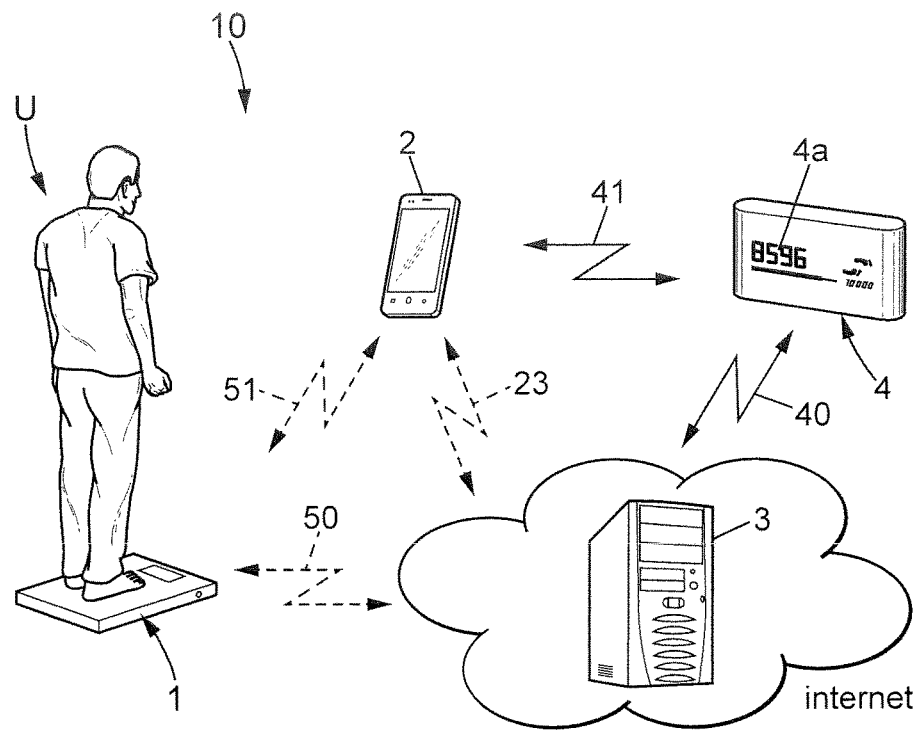
FIG. 1 is a general view of a system in which the method according to the invention can be implemented.

FIG. 1 shows an exemplary system 10 in which the method of the invention can be implemented.

The system includes an electronic scale 1 of the type capable of measuring the total weight of the individual U and also of measuring the body fat percentage of said individual. In addition, the electronic scale includes a wireless communication interface 5, which can be either in the form of a WiFi interface or a Bluetooth™ interface, or an interface capable of operating in multiple modes of wireless communication.

The system further comprises a remote entity capable of collecting information originating from the electronic scale.

According to a first solution, said remote entity may be a smartphone or a tablet or a laptop or desktop computer, meaning a device within the user's environment, represented by the reference 2 in FIG. 1, and connected to the scale by means of a short-range wireless link 51.

In a second solution, the remote entity is a data server type of computer 3 able to retrieve data from the electronic scale 1 directly via a wireless connection 50 of significant range. The data server in question is common to a plurality of users; it is usually connected to one or more high-speed Internet connections and has high computing power. It should therefore be considered as a resource shared by a set of users and where appropriate by a service provider providing the method as will be described below.

It should be noted that the system 10 may include both a data server 3 as described above and a smartphone 2 in the possession of the user U. The data sent up from the household scale can travel via the smartphone which sends them on to the data server 3 over a conventional Internet connection 23 as is known.

In addition, in the example shown in FIG. 1, the system comprises a personal activity monitor 4 such as the product "Pulse™" from the WITHINGS® company; such an activity monitor comprises various sensors for measuring the physical activity performed by the person wearing the monitor and a display 4a for showing the user U data related to the exercise.

The activity monitor 4 can receive data directly from the data server 3 via connection 40 or from the user's smartphone 2 via connection 41.

We will now describe the method with reference to FIGS. 1 to 4. The method is based on the use of a plurality of prior weighings of the individual U concerned, each weighing providing the total weight and the body fat percentage. These prior weighings (step /a/ of the method) may be all the weighings obtained during the previous week, or during the previous fortnight, or during the previous month, or during some other period. For each weighing, the total weight and if possible the body fat percentage are recorded.

Simple weighings that do not include the body fat percentage are still usable, as will be seen below, for defining a current trend in the total weight, or even as the most recent known weight reading.

These weight data are sent to the remote entity, which may be the smartphone 2 of the individual or the shared data server 3. The weight data may advantageously be timestamped.

Note, however, that in an alternative not shown in the figures, these data can be stored locally and processed locally in the scale, according to the method described below.

Advantageously, the method will use the most recent weighings to determine a current trend in the total weight of the individual; for example, data collected over the last five days allow deducing a current upward or downward trend in the total weight of the individual U (optional step /a1/). In addition, a value corresponding to the most recent weight reading for the user can be determined, using the most recent or the two or three most recent weighings.

Figure 2:
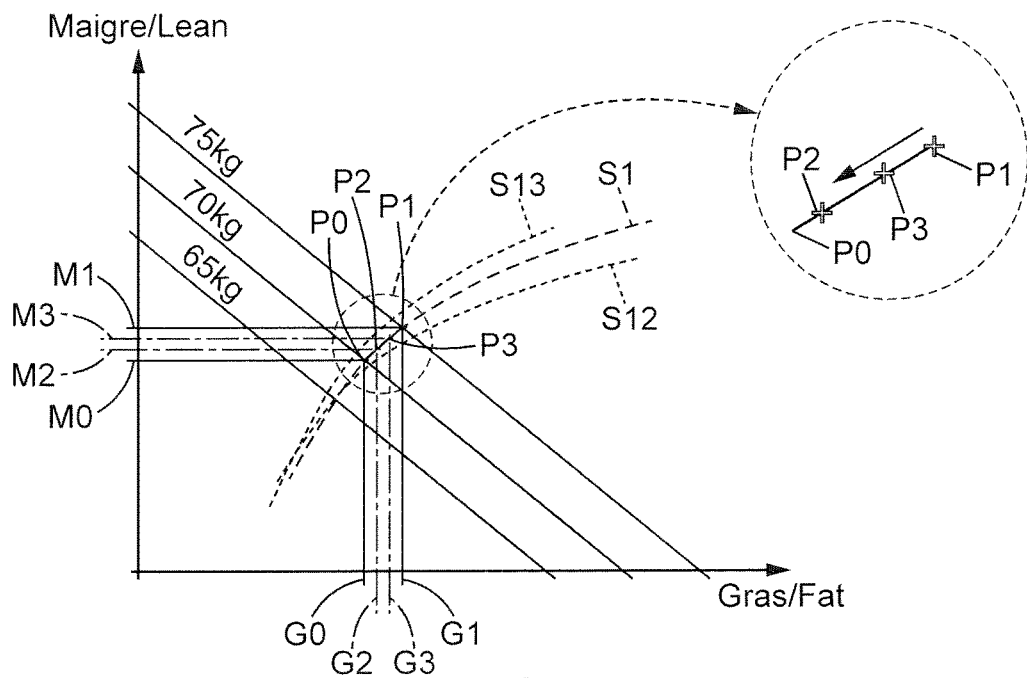
FIG. 2 shows a characteristic weight curve for a particular individual.

The plurality of previous weighings advantageously allows, because of the differences observed between weighings, at least partially determining (step /b/ of the method) a characteristic curve for the individual, of which an example is shown in FIG. 2.

The illustrated curve represents the fat body mass on the x-axis and the lean body mass on the y-axis. Regression lines at constant total weight are also shown. In the example shown, during the preceding days or weeks, the weighings gave a total weight varying between 70 and 75 kg. Knowing the body fat percentage allows at least partially plotting the characteristic curve S1 that relates the fat body mass to the lean body mass (portion P0-P1).

Alternatively, note that the characteristic curve could simply represent the fat body mass as a function of the total weight, the lean body mass then being deduced from the two items of information connected by the curve. More generally, two of the three following numbers: total weight, fat body mass, and lean body mass, are interconnected by a characteristic function specific to the individual, it being possible to deduce the third value from the first two. Therefore, the presentation represented in FIG. 2 is only one of several possibilities for representing the characteristic function specific to the individual, which in the current case is a characteristic curve relating the lean body mass and fat body mass.

Depending on the representation options chosen, the lean body mass preferably includes the mass of water (H2O) contained within the individual's body.

It should be noted here that the characteristic curve S1 is specific to the individual concerned; another individual has the curve labeled S12, while a third individual has the curve labeled S13. The curve is deduced from previous weighings of the individual in question and does not require knowledge of general statistical data concerning the population such as size, age, gender, ethnicity, etc.

Knowledge of the characteristic curve S1 specific to the individual will allow giving him or her the most appropriate recommendations when a target total weight to be reached by the end of a target period is set. For example, if at the current time T1, the individual weighs 75 kg (P1, corresponding to the most recent weighing) and wishes to reach 72 kg in two weeks (weight P2 at time 'T2'), then he or she wants to lose 3 kg in two weeks.

The determination of the target total weight represents step /c/ of the method. This target total weight can be entered on the individual's smartphone 2, or through a Web interface connected to the data server 3.

First, the difference between the total target weight and the last known recorded weight is calculated, or in other words P2-P1, which constitutes what is referred to as the "total weight change target." The following paragraphs concern the conversion of this total weight change target into a target number of calories to burn (or gain).

Note that generally this involves losing weight, but the reverse case is not excluded, which is why we refer to 'weight changes' rather than 'weight loss'. Similarly, the target number of calories to be burned or gained is a signed number.

According to a first possibility, the characteristic curve is used in a very simple manner by linearizing it around the usual weight of the individual. This defines, for a target weight loss unit (1 kilogram), the exact change in fat body mass and lean body mass corresponding to the individual concerned. Then the conversion coefficients KM, KG are used to obtain the equivalent in calories of the change in fat body mass and the equivalent in calories of the change in lean body mass.

1 Kg of fat body mass=KG (calibrated value of between 8000 and 11000 cal)

1 Kg of lean body mass=KM (calibrated value between 1000 and 6000 cal, according to the proportion of mass of water)

Then, the two coefficients are weighted according to the relative proportion of lean and fat body mass which is given by the slope of the characteristic curve S1, thereby obtaining an aggregate conversion coefficient KT that maps a target weight loss unit to a target number of calories to burn for 1 kg, which can be expressed as:

$$KT = \alpha \cdot KG + \lambda \cdot KM$$

We will then use said aggregate coefficient KT to convert any target total weight loss for the individual concerned into a target number of calories to burn.

According to a second possibility, by using the characteristic curve, the target total weight loss is converted into a loss of fat body mass (G1-G2) and a loss of lean body mass (M1-M2) (step /d/ of the method); this conversion essentially depends on the slope of the characteristic curve at point P1, but is specific to the individual.

In the next step, the target change in fat body mass is converted into calorie values (coefficient KG mentioned above) and the target variation in lean body mass into calorie values (coefficient KM mentioned above). These two values are then added to obtain a total target calorie change.

This conversion of the target weight loss into calories can be done using the gross (absolute) value, or in other words without considering the current trend at time T1.

Figure 3:
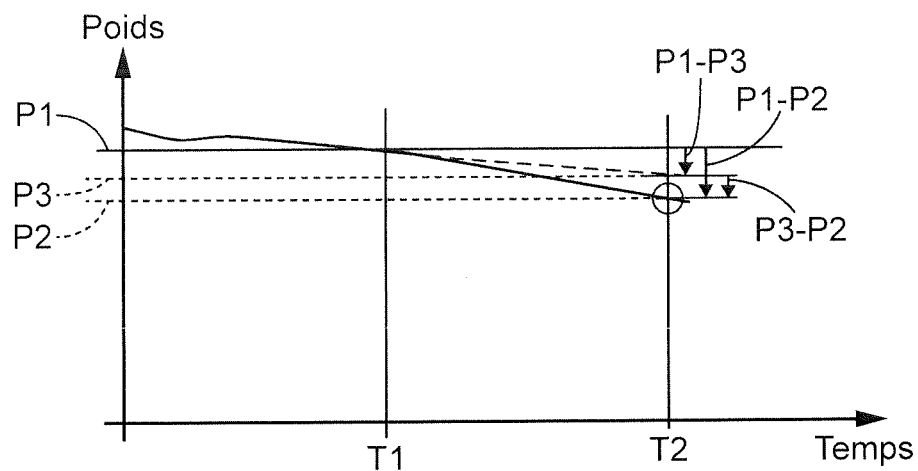
FIG. 3 shows a graph of the individual's change in weight over time.

However, advantageously and optionally, the current trend determined in step /a1/ can be taken into account. Specifically, as shown in FIG. 3, it is considered that if the user does not change his eating habits and exercise, he or she will reach point P3 (for example 73.5 kg in the example shown). We will then work with the net weight loss value (P3-P2) rather than the gross P1-P2.

More specifically, in this case we want to provide the user only with instructions for changing habits, therefore deduced only on the basis of values between point P3 and point P2.

According to the first possibility mentioned above, the aggregate coefficient KT is applied to the difference P3-P2, and a relative target number of calories is obtained.

In the second possibility mentioned above, the amounts G3-G2 and M3-M2 are deduced from the characteristic curve S1; then the amounts G3-G2 and M3-M2 are converted into calories, still using the conversion coefficients KM and KG.

These are referred to as relative instructions (meaning a change relative to current habits).

In a subsequent step /e/, the user is provided with absolute or relative instructions concerning the physical activity to be performed within the next few days.

This involves known calculations for converting the target number of calories to burn into a period of exercise, according to the type of exercise concerned, referring to data known as MET (Metabolic Equivalent of Task). Conventionally, additional parameters including gender, age, and height of the individual are used to better define the coefficients for converting between the number of calories to burn and a given duration of physical activity.

In a very simple solution, the activity used is walking, the most common and accessible. The solution then involves defining a number of steps to be carried out, for example on a daily basis.

Advantageously, if calculating with net values (relative calculation taking into account the current trend), one simply provides an additional number of steps to be taken relative to current habits.

However, if additional data concerning the individual are available such as current eating habits, then it is possible to give absolute exercise instructions.

If, for example, the average number of steps taken each day is known for last three weeks, then absolute instructions can be given by adding the number of additional steps to be taken (resulting from the calculation explained above) beyond the average daily number of steps taken in the past.

Figure 4:
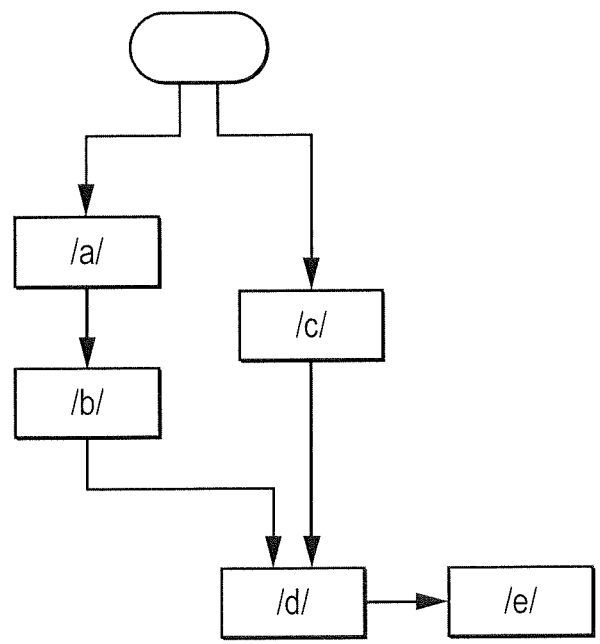
FIG. 4 illustrates the steps of the method implemented according to the invention.

For the method as symbolically represented in FIG. 4, one will note that step /c/ can be done in parallel with steps /a/ and /b/, step /d/ can be performed according to several possibilities as mentioned above, and step /e/ consisting of providing instructions to the user can take many forms.

In the current example, the instructions can be given to the user on a personal activity monitor 4. According to another embodiment, there may not be a personal activity monitor and the instructions can be given to the user on a personal device, for example a smartphone, in which case some or all of the method is implemented by said smartphone.

In another embodiment, the personal device is the scale itself. A scale can thus be offered with extended functionalities able to perform some or all of the method.

It is therefore understood that the method as described can be implemented in any manner in one or more processing units and/or display units, in a non-limiting manner.

The invention claimed is:

1. A method for providing personalized recommendations to a user, relating to monitoring his or her weight, comprising the steps, executed in the following order, of:
   /a/ obtaining, by means of an electronic scale, configured to measure the total weight and the body fat percentage of the user and to send the data to a remote unit by means of a wireless communication interface, a plurality of prior weighings of the user, each weighing giving the total weight and the body fat percentage,
   /b/ deriving from the prior weighings, by means of the remote unit capable of performing calculations, configured to collect and process the collected data originating from the electronic scale, a characteristic curve specific for the user concerned by associating at least two of the following three quantities: total weight, fat body mass, and lean body mass, over at least one total weight range,
   /c/ obtaining, by means of the remote unit, a target total weight for the user to be achieved by the end of a target period, and therefore a target total weight change relative to the latest known total weight reading,
   /d/ deducing, by means of the remote unit, from steps /b/ and /c/ a target number of calories to burn, corresponding to target changes in the fat body mass and lean body mass deduced from said total weight change by means of the characteristic curve specific for the user concerned,
   /e/ providing, by means of a personal device connected to the remote unit, the user with exercise and/or diet instructions based on said target number of calories to burn,
   whereby the user can receive, on the personal device, personalized recommendations for achieving the target weight.

2. The method according to claim 1, wherein step /a/ further comprises
   /a1/ determining a current trend concerning the total weight of the user, by means of the most recent weighings,
   and wherein step /d/ further comprises
   /d1/ deducing, from the target total weight change, the change expected at the end of the target period, due to the current trend, the target number of calories to burn then being a relative target number of calories, such that the instructions given to the user are instructions on changing relative to recent habits rather than absolute instructions.

3. The method according to claim 1, wherein additional parameters including gender, age, and height of the user are also used in converting in step /e/ the target number of calories to burn into exercise duration for the user concerned.

4. The method according to claim 1, wherein the instructions are provided in the form of a number of steps to be taken.

5. The method according to claim 4, wherein, in step /e/, the instructions of a number of steps to be taken are added to an average daily number of steps taken in the past.

6. The method according to claim 1, wherein the characteristic curve (S1) is approximated by a straight line within a habitual weight range of the user.

7. The method according to claim 1, wherein the remote unit is a data server.

8. The method according to claim 1, wherein the remote unit is a smart mobile device.

9. The method according to claim 8, wherein the remote unit is combined with the personal device, the personal device being a smartphone, whereby the method is performed by a system comprising only the electronic scale and the personal device.

10. The method according to claim 8, wherein the remote unit is combined with the personal device, the personal device being a tablet, whereby the system comprises only the electronic scale and the personal device.

11. The method according to claim 1, wherein the personal device is a personal activity monitor and the instructions are displayed on it as a number of steps to be taken.

12. The method according to claim 1, wherein the personal device consists of the electronic scale itself.

* * * * *